United States Patent [19]
Goodson et al.

[11] Patent Number: 6,117,142
[45] Date of Patent: *Sep. 12, 2000

[54] EMBOLIC COIL HYDRAULIC DEPLOYMENT SYSTEM WITH IMPROVED SYRINGE INJECTOR

[75] Inventors: Harry B. Goodson, Ft. Lauderdale; Brett E. Naglreiter, Hollywood, both of Fla.

[73] Assignee: Cordis Corporation, Miami Lakes, Fla.

[*] Notice: This patent is subject to a terminal disclaimer.

[21] Appl. No.: 09/258,678

[22] Filed: Feb. 25, 1999

Related U.S. Application Data

[60] Provisional application No. 60/077,404, Mar. 10, 1998.

[51] Int. Cl.⁷ .................................................. A61F 11/00
[52] U.S. Cl. ............................................... 606/108
[58] Field of Search ...................... 606/108, 200, 606/191; 604/14, 266

[56] References Cited

U.S. PATENT DOCUMENTS

| | | |
|---|---|---|
| 2,853,070 | 9/1958 | Julliard . |
| 3,334,629 | 8/1967 | Cohn . |
| 3,353,718 | 11/1967 | McLay . |
| 4,512,338 | 4/1985 | Balko et al. . |
| 4,743,230 | 5/1988 | Nordquest . |
| 4,832,692 | 5/1989 | Box et al. . |
| 4,919,121 | 4/1990 | Rydell et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,137,514 | 8/1992 | Ryan . |
| 5,167,624 | 12/1992 | Butler et al. ........................ 606/191 |
| 5,168,757 | 12/1992 | Rabenau et al. . |
| 5,217,484 | 6/1993 | Marks . |
| 5,234,437 | 8/1993 | Sepetka . |
| 5,250,071 | 10/1993 | Palermo . |
| 5,261,916 | 11/1993 | Engelson . |
| 5,263,964 | 11/1993 | Purdy . |
| 5,304,195 | 4/1994 | Twyford, Jr. et al. . |
| 5,312,415 | 5/1994 | Palermo . |
| 5,334,210 | 8/1994 | Gianturco . |
| 5,336,183 | 8/1994 | Greelis et al. . |
| 5,342,304 | 8/1994 | Tacklind et al. . |
| 5,350,397 | 9/1994 | Palermo et al. . |
| 5,382,259 | 1/1995 | Phelps et al. . |
| 5,403,292 | 4/1995 | Ju ........................................ 604/264 |
| 5,443,478 | 8/1995 | Purdy . |
| 5,470,317 | 11/1995 | Cananzey et al. . |
| 5,578,074 | 11/1996 | Mirigian . |
| 5,582,619 | 12/1996 | Ken . |
| 5,601,600 | 2/1997 | Ton . |
| 5,609,608 | 3/1997 | Benett et al. . |
| 5,647,847 | 7/1997 | Lafontaine et al. . |
| 5,853,418 | 12/1998 | Ken et al. . |

FOREIGN PATENT DOCUMENTS

| | | | |
|---|---|---|---|
| 0717969 | 6/1996 | European Pat. Off. ............... | 606/108 |

OTHER PUBLICATIONS

Brochure entitled, "Guglielmi Detachable Coils," by Boston Scientific.
Label of IDC–18 Interlocking Detachable Coil by Target Therapeutics, Inc.
Brochure entitled, "Detachable Coil System," by Cook.
Brochure entitled, "Basic25™ Inflation Device," by Merit Medical Systems, Inc.
Brochure entitled, "MonarchAP® Inflation Device," by Merit Medical Systems, Inc.
Label of B. Braun Inflation Device Kit by B. Braun Medical Inc.

*Primary Examiner*—Jeffrey A. Smith
*Assistant Examiner*—Eduardo C. Robert

[57] ABSTRACT

A medical device for placing an embolic coil at a preselected location within a vessel comprising a positioning catheter having a distal tip for retaining the embolic coil which when pressurized with a hydraulic fluid expands outwardly to release the coil at the preselected position. The fluid is injected with a syringe having a pressure monitor which is contained within the body of the syringe.

5 Claims, 3 Drawing Sheets

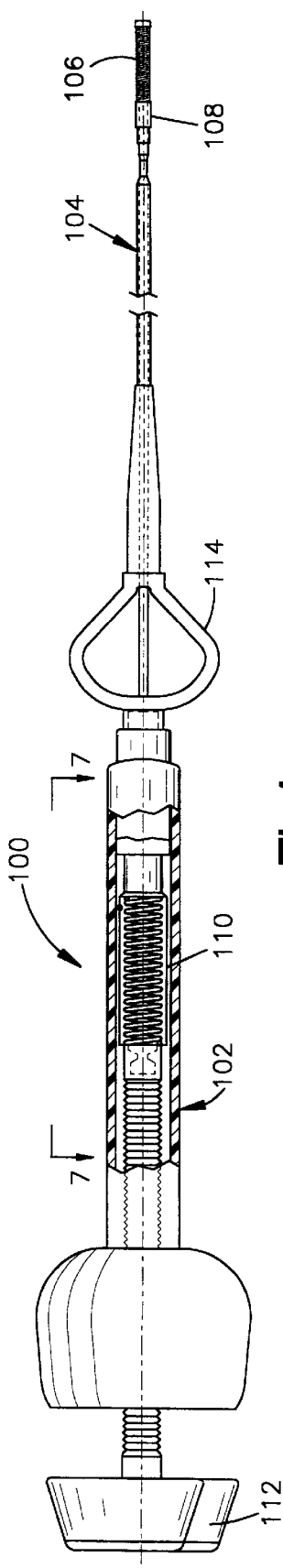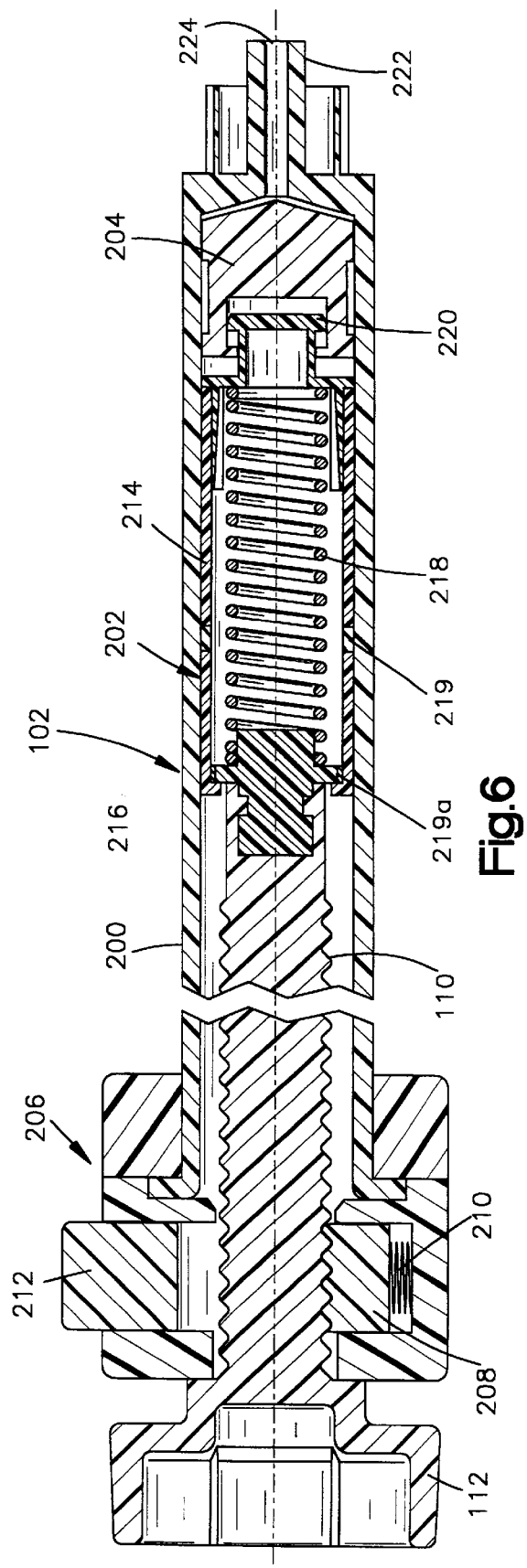

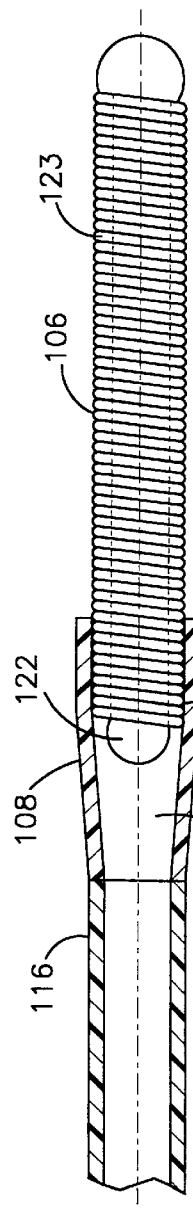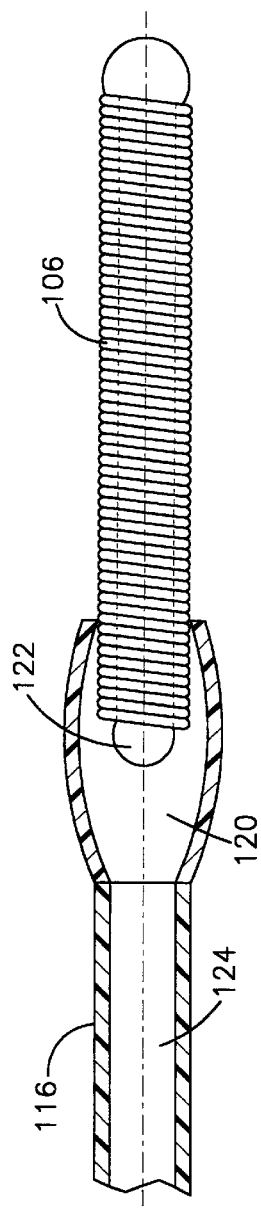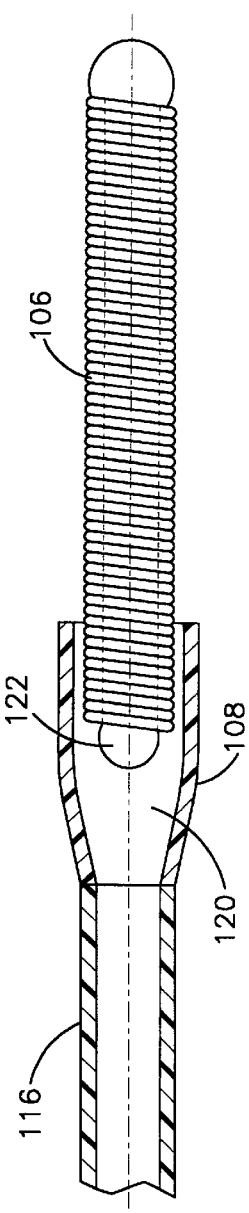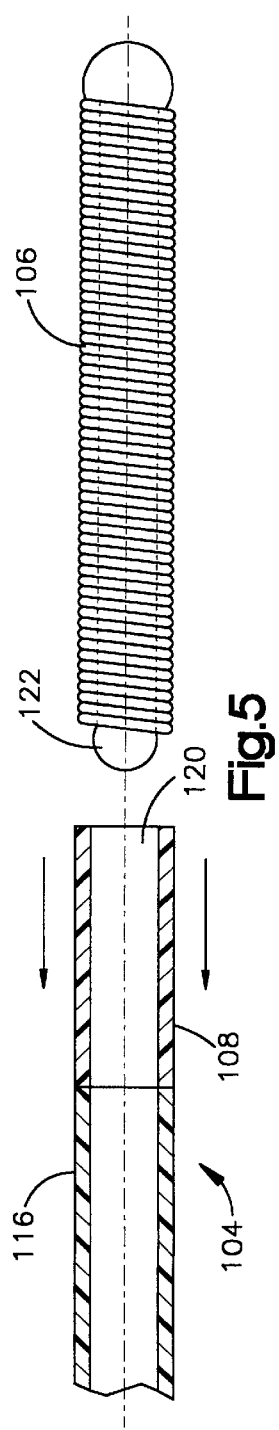

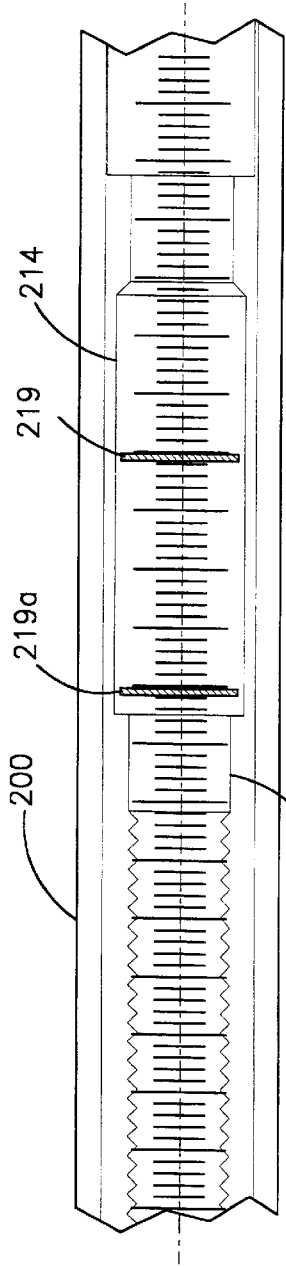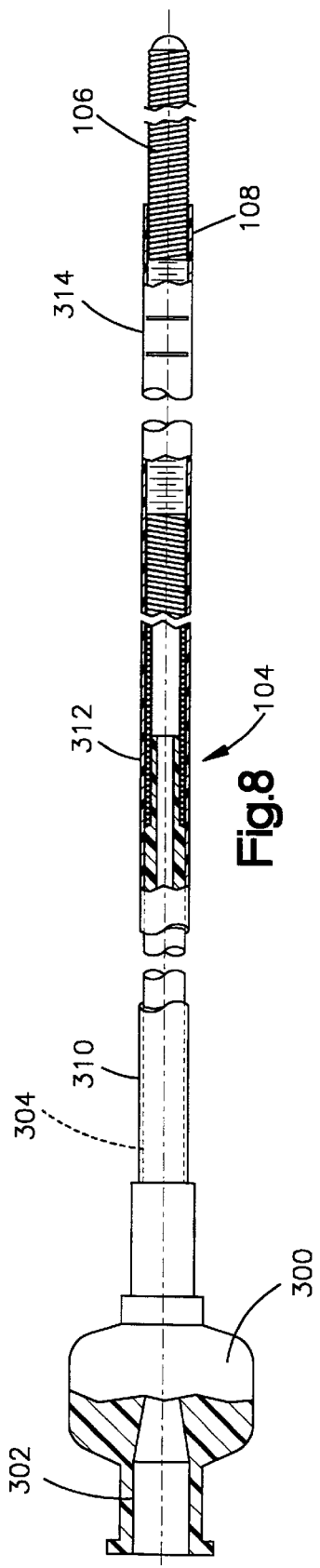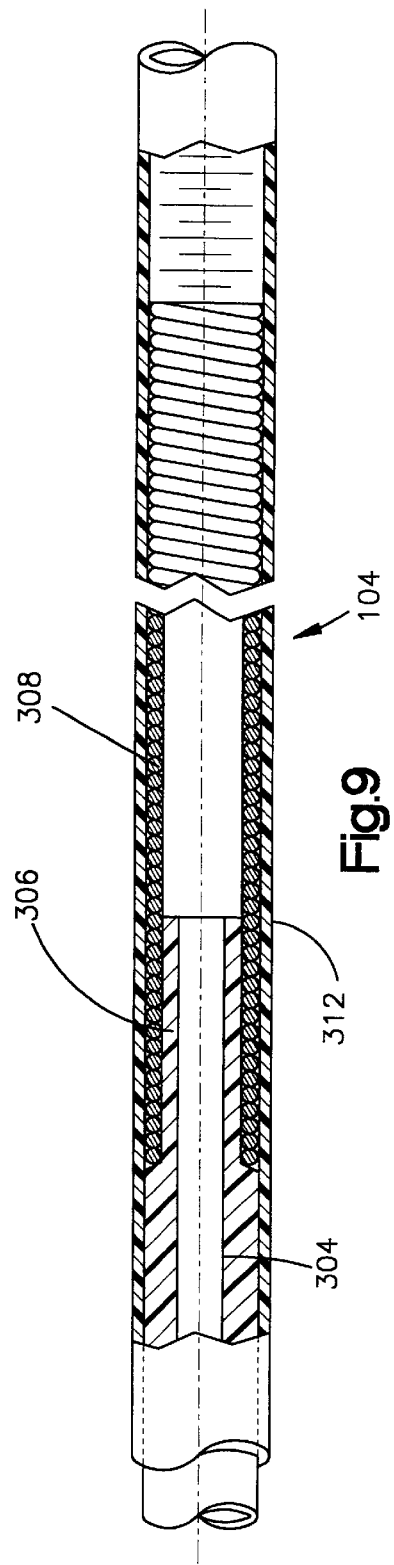

EMBOLIC COIL HYDRAULIC DEPLOYMENT SYSTEM WITH IMPROVED SYRINGE INJECTOR

This application claims the benefit of U.S. Provisional Ser. No. 60/077,404 filed Mar. 10, 1998.

BACKGROUND OF THE INVENTION

1. Field of the Invention

The present invention relates to a medical device for placing an embolic coil at a preselected location within a vessel of the human body, and more particularly, relates to a catheter having a distal tip for retaining the embolic coil in order to transport the coil to a preselected position within the vessel and a control mechanism for releasing the embolic coil at the preselected position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, veins, Aneurysms, Vascular Malformations And Arteriovenous Fistulas." These patents disclose devices for delivering embolic coils to preselected position within vessel of the human body in order to treat aneurysms or alternatively to occlude the blood vessel at the particular location.

Coils which are placed in vessels may take the form of helically wound coils, or alternatively, may be random wound coils, coils wound within other coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, the proximal tips of embolic coils have been placed within the distal end of a catheter and when the distal end of the catheter is properly positioned the coil may then be pushed out of the end of the catheter with, for example a guidewire, to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to be detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate element which extends throughout the length of the catheter with the resulting stiffness of the catheter.

Still another coil positioning system for placing an embolic coil at a preselected location within a vessel of the human body includes a catheter for retaining an embolic coil at the distal end of the catheter in order to transport the coil to the preselected position. When the coil has been properly placed, a hydraulic fluid is applied to the catheter to thereby cause the distal tip of the catheter to expand thereby releasing the embolic coil at the preselected position. Such a coil positioning system is disclosed in U.S. patent application Ser. No. 09/177,848, entitled, "Embolic Coil Hydraulic Deployment System." This patent application is assigned to the same assignee as the present application.

U.S. Pat. No. 5,336,183 discloses a syringe having a pressure responsive gage mounted along the side of the syringe for measurement of the pressure developed by the syringe, however, with a device of this type there is a large open area distal of the syringe plunger for retaining air. It would be difficult to purge all of the air out of such a syringe.

SUMMARY OF THE INVENTION

The present invention is directed toward a vascular occlusive coil deployment system for use in placing an embolic coil at a preselected site within a vessel which includes an elongated, flexible catheter having a distal tip for retaining the coil so that the coil may be moved to the preselected position within the vessel. The catheter has a lumen which extends therethrough the length of the catheter and also includes a distal end which is formed of a material having a durometer such that when a fluid pressure of about 90 to 450 pounds per square inch (psi) is applied to the interior of the catheter, the walls of the distal tip expand outwardly, or radially, to thereby increase the lumen of the distal tip of the catheter. The proximal end of the embolic coil is placed into the lumen of the distal tip of the catheter and is retained by the distal tip of the catheter. A hydraulic injector, which takes the form of a syringe, is coupled to the proximal end of the catheter for applying a fluid pressure to the interior of the catheter. When the coil is placed at a desired position within a vessel, fluid pressure is then applied to the interior of the catheter by the syringe to thereby cause the walls of the distal tip to expand outwardly to thereby release the coil for placement in the vessel. The syringe includes a very precise pressure monitoring system which is contained within the body of the syringe for measuring the hydraulic pressure applied by the syringe so that sufficient pressure may be applied by the syringe to disengage the embolic coil. Also, the pressure monitoring system provides a visual indication (loss of pressure) upon the release of the embolic coil from the deployment system. With the syringe of the present invention having a in-line pressure monitor it is very simple to remove or purge all of the air from the syringe prior to use.

BRIEF DESCRIPTION OF THE DRAWINGS

FIG. 1 is a partially sectioned view of the hydraulic vascular occlusive coil deployment system of the present invention;

FIG. 2 is an enlarged partially sectioned view showing the distal end of the coil deployment system prior to deployment of the coil;

FIG. 3 and 4 illustrate the sequential steps in the radial expansion of the distal tip of the coil deployment system as the embolic coil is released;

FIG. 5 illustrates the distal tip of the coil deployment system after release of the embolic coil;

FIG. 6 is a partially sectioned view showing the details of the syringe with a pressure monitor;

FIG. 7 is a plan view of the syringe which illustrates the in-line pressure gage;

FIG. 8 is a partially sectioned view showing the details of the catheter portion of the coil delivery system; and, FIG. 9 is partially sectioned view of a portion of FIG. 8.

DESCRIPTION OF A PREFERRED EMBODIMENT

FIG. 1 generally illustrates the vascular occlusive coil deployment system 100 which is comprised of a hydraulic injector or syringe 102, coupled to the proximal end of a catheter 104. An embolic coil 106 is disposed within the lumen of the distal end 108 of the catheter. The proximal end of the coil 106 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114.

FIG. 2 illustrates in more detail the distal end of the catheter 104. The catheter 104 includes a proximal section 116 and the distal section 108. The proximal section 118 of the embolic coil 106 is disposed within the distal section 108 of the catheter and is tightly held within the lumen 120 of this distal section 108 prior to release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a weld bead or seal plug 122 which is disposed in a lumen 123 which lumen extends throughout the length of the coil 106. The seal plug 122 serves to prevent the flow of fluid through the lumen of the coil 106 so that when the coil 106 is placed in fluid-tight engagement with the lumen 120 the coil serves to provide a fluid-tight seal at the distal end of the catheter 104. Adjacent turns of the coil 106 at the proximal end 118 of the coil are preferably continuously welded together so that the welded turns of the coil in conjunction with the plug seal 122 provide a generally unitary structure which serves to plug or seal the distal end of the catheter in a fluid tight relationship yet is still very flexible.

A liquid silicon material (not shown) may be injected to fill the lumen of the proximal portion of the coil. The silicone material is then allowed to cure in order to further seal the proximal end of the coil to prevent fluid leakage through the turns of the coil. Also, as may be appreciated, instead of spot welding adjacent turns of the coil, the adjacent turns may be bonded by various other means such as, for example, by glueing or being attached by wrapping with thread.

Preferably, the proximal section 116 and the distal section 108 of the catheter 104 are formed of materials having different durometers. The proximal section 116 is preferably formed of Vestimed material having a durometer in a range of about 62D to 75D. The proximal section is sufficiently flexible to transverse the vasculature of the human body, but is sufficiently rigid such that when a fluid pressure of approximately 90 to 450 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 90 to 450 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25D and 55D with a durometer of 40D being the preferred durometer.

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the coil 106 becomes disengaged from the lumen of the distal section 108 and the coil is then released from the catheter and is deployed at that location within the vessel.

As illustrated in FIG. 5, when the coil 106 has been released from the catheter 104 the catheter may then be withdrawn leaving the coil positioned at the desired site.

FIG. 6 illustrates in more detail the syringe 102 which takes the form of a syringe having a volume preferably of between 3 and 10 cubic centimeters for injection of a fluid into the catheter 104 for deployment of the coil 106. The syringe includes an outer syringe barrel 200, the threaded piston 110 which is attached through an in-line internal pressure gage 202 to a fluid plunger 204. The outer barrel 200 of the syringe is formed of a translucent or transparent material in order that the internal pressure gage 202 may be visually inspected during operation.

As illustrated, the threaded piston, engages a thread engagement mechanism 206 so that the piston 110 may either be manually pushed into the outer barrel 200, or may alternatively be moved into the outer barrel by rotation of the handle 112 through the thread engagement mechanism 206. The engagement mechanism 206 is comprised of a movable threaded block 208 which is biased into contact with the threaded piston 110 by a helical spring 210. A thread engagement knob 212 is coupled to the thread block 208 such that the thread block 208, which is normally in engagement with the threaded piston, may be moved downward by pressure being applied to the thread engagement knob 212 to release the thread block 208 from the threaded piston 110 to thereby allow the handle 112 to be manually pushed into the outer barrel 200.

The distal end of the threaded piston 110 is coupled to an internal pressure gage 202, which is in turn coupled to the plunger 204. More particularly, the pressure gage 202 includes a cylindrical gage housing 214, a bearing assembly 216 which slidably engages the interior of the cylindrical gage housing 214 and a calibrated helical spring 218 for biasing the bearing assembly 216 to a most proximal position within the cylindrical gage housing 214. The distal end of the gage housing 214 is coupled through a bracket assembly 220 to the plunger 202.

The cylindrical gage housing 214 is formed of a translucent plastic material so that the relative position of the bearing assembly 216 may be monitored in order to provide an indication of the hydraulic pressure being applied by the syringe. As illustrated in FIG. 7 and 8, a pressure indicator mark 219 is placed on the outer circumference of the cylindrical gage housing 214 at a preselected position. In addition, a pressure indicator marker 219 is placed on the outer circumference of the bearing assembly 216 in order to permit the user to determine the relative position of the bearing assembly 216. As illustrated in FIG. 7, the circumferential pressure indicator markers 219, 219*a* appear as straight lines when viewed by an operator.

The outer barrel 200 of the syringe 102 is connected at its distal end to a luer connector 222 which includes an outlet port 224 for connecting the syringe to the coil deployment catheter. The outer barrel 200 of the syringe 102 is formed of a translucent plastic material.

In operation, the syringe 102 may be operated by simply turning the handle 112 in a clockwise direction in order to move the plunger 202 in a distal direction in order to infuse fluid through the outlet port 224. Alternatively, by applying pressure to the thread engagement knob 212 it is possible to release the thread block 208 thereby making it possible to simply push the handle 112 in a direction toward the distal end of the syringe in order to infuse fluid from the outlet port 224.

The internal pressure gage 202 serves to continuously monitor the fluid pressure being applied by the syringe to the coil deployment catheter. Accordingly, as the piston 110 is moved toward the distal end of the syringe in order to infuse fluid into the coil deployment system, an equal and opposite pressure will be applied to the plunger 204 which, in turn, causes the spring 218 to become compressed. As the threaded piston 110 slides into the gage housing 214, the spacing between the pressure marker 219A on the bearing assembly 216 and the pressure marker 219 on the gage housing 214 begin moving closer together. At the point that the housing pressure marker 219 appears directly over the bearing assembly marker 219A, the pressure applied to the fluid has reached the calibrated pressure for the particular syringe. As may be appreciated, the pressure marker 219 on the gage housing may be applied at any preselected position along the surface of the gage housing which corresponds to a desired calibrated pressure measurement by the pressure gage.

Upon release of the embolic coil 106, there is a release of the pressure developed by the plunger 204 with the result that the pressure indicators 219, 219A separate. When these marks 219, 219A separate, the operator has a visual indication that the coil 106 has been released from the deployment system.

FIG. 7 is a partial plan view of the syringe 102 which generally illustrates the position of the pressure indicator marker 219, 219A prior to pressure being applied by the syringe. Again, at the point in which the syringe reaches its calibrated pressure, indicator marker 219 will appear to be directly over the indicator marker 219A. When the pressure developed by the syringe is released, i.e., upon deployment of the embolic coil 106, the pressure indicators 219, moved back to their initial position as shown in FIG. 7.

FIGS. 8 and 9 illustrate in more detail the catheter 104 which is comprised of a luer hub 300 having a lumen 302 extending therethrough. The hub 300 is of a slightly different design from the design of the hub 114 of FIG. 1. A stainless steel hypo-tube 304 extends from the hub 114 and, as illustrated in FIG. 9, the distal end of the hypo-tube 304 is grounded down to provide a step-down portion 306. A helical support coil 308 surrounds the step-down portion 306 of the hypo-tube 304 and is bonded to the hypo-tube, and also extends to a position slightly proximal to the distal end of the catheter 104. A polymer tubing 310 is placed around the hypo-tube and the support coil 308 and extends to the distal end of the catheter. The polymer tube is preferably comprised of 3 sections of differing durometers. Preferably, the proximal section 312 of the tube 310 is formed of a polymer having a durometer of 75D, an intermediate section 314 is formed of a polymer having a durometer of 62D, and the distal section 108 is formed of a polymer having a relatively soft polymer having a durometer of 40D. The proximal tip of the embolic coil 106 engages the lumen of the distal section 108 and is retained by the distal section until fluid pressure is applied to the catheter 104 to thereby cause the relatively soft distal section 108 to expand and thereby release the coil 106.

The proximal section 312, the intermediate section 314, and the distal section 108 are fused together by having heat applied to the joints of these sections. As is illustrated in FIG. 8, the support coil 308 terminates at its distal end at a position along the distal section 108 slightly proximal of the proximal end of the embolic coil 106. The catheter 104 is preferably of a diameter of approximately 0.010 to 0.018 inches and is of a length of approximately 195 centimeters. The hypo-tube 304 has an outside diameter of approximately 0.007 to about 0.013 inches and has a length of about 100 centimeters. The proximal section 312 is of a length of approximately 170 centimeters, the intermediate section is of a length of approximately 0.5 centimeters, and the distal section 108 is of a length of about 1 centimeter.

As may be apparent, the catheter 104 exhibits six different levels of flexibility. The proximal section 312 over the hypo-tube 304 provides a relatively stiff section which resists kinking and enhances the ability of the catheter to be pushed through a vessel, the portion of the proximal section 312 over the region with the stepped down hypo-tube and support coil provides a more flexible region than the most proximal 312 over the unground hypo-tube, the proximal section 312 over the region of the support spring only is more flexible than the previously described section, and the 62D and 40D sections provide increased flexibility over their more proximal sections of the catheter. Finally, the most distal tip being formed of 40D material and having no underlying support coil, provides a very soft and flexible distal tip for retaining and releasing the embolic coil 106. Accordingly, the coil deployment catheter 104 of the present invention provides a catheter of improved "pushability" as well as a catheter having very smooth transition zones with a very flexible distal tip for navigating through tortuous vasculature of the human body.

With the vascular occlusive coil deployment system of the present invention it is possible to place an embolic coil very precisely at a desired location within a vessel. Once the coil has been placed at a desired location by use of the catheter, the catheter tip may be activated by applying a hydraulic pressure to the interior of the catheter to thereby cause the catheter tip to expand and release the coil to thereby deposit the coil very accurately at the desired location.

As is apparent, there are numerous modifications of the preferred embodiment described above which will be readily apparent to one skilled in the art, such as many variations and modifications of the syringe for applying a fluid pressure to the interior of the catheter, including many other types of fluid pressure generating systems for increasing the pressure within the interior of a catheter. These modifications would be apparent to those having ordinary skill in the art to which this invention relates and are intended to be within the scope of the claims which follow.

What is claimed is:

1. A vaso-occlusive coil deployment system for use in placing a coil at a preselected site within a vessel comprising:

an elongated flexible catheter having a wall and a lumen extending throughout the length of the catheter, said catheter further having a proximal section and a distal section, said distal section of the catheter being formed of a material having a durometer which exhibits the characteristic that when a fluid pressure is applied to the interior of the catheter the walls of the distal section of the catheter expand outwardly;

an embolic coil being disposed in fluid-tight engagement within the lumen of the distal section of the catheter;

a syringe coupled to the proximal section of the catheter for applying a fluid pressure to the interior of the catheter to thereby cause the distal section of the catheter to expand outwardly to thereby release the embolic coil; and, said syringe comprising a syringe housing having a cylindrical wall and a lumen extending throughout the length of the catheter, said syringe housing further having a proximal end and a distal end, and having a port at the distal end for communicating with the proximal section of the elongated flexible catheter, a piston having an outer surface, said piston being movably mounted within the lumen and extending out of the proximal end of the syringe housing, a plunger movably mounted in the lumen at the distal end of the syringe for applying a fluid through the port, and a pressure gage for providing an indication of the amount of pressure being applied to the plunger by the piston.

2. A vaso-occlusive coil deployment system as defined in claim 1, wherein said pressure gage is comprised of a gage housing having a cylindrical wall, said gage housing being slidably mounted coaxially within the syringe housing, the gage housing having a lumen extending therethrough, a gage plunger slidably mounted within the lumen of the gage housing, bias means for urging the gage plunger toward one end of the gage housing, the other end of the gage housing being fixedly attached to the syringe plunger, and the gage plunger coupled to the movable piston so that movement of the gage plunger within the gage housing is indicative of pressure applied to the syringe plunger by the movable piston.

3. A vaso-occlusive coil deployment systems as defined in claim 2, wherein the gage housing is coaxial with the syringe housing.

4. A vaso-occlusive coil deployment system as defined in claim 3, wherein the wall of the syringe housing is translucent, the wall of the gage housing is transparent, a pressure marker is disposed at a preselected position on the gage housing, and a pressure marker is placed on the gage plunger.

5. A vaso-occlusive coil deployment systems as defined in claim 4, wherein the syringe includes an injector handle coupled to the proximal end of the piston, the piston includes a continuous threaded portion along the outer surface of the piston, and a thread engagement mechanism is disposed on the proximal end of the cylindrical housing of the syringe for engagement with the threaded portion of the piston.

\* \* \* \* \*